United States Patent
Belmant et al.

(10) Patent No.: US 6,624,151 B1
(45) Date of Patent: Sep. 23, 2003

(54) COMPOUNDS SELECTIVELY INHIBITING GAMMA 9 DELTA 2 T LYMPHOCYTES

(75) Inventors: Christian Belmant, Blagnac (FR); Marc Bonneville, Vertou (FR); Marc Alix Peyrat, Sebastien (FR); Jean-Jacques Fournie, Corronsac (FR); Alan P. Kozikowski, Princeton, NJ (US)

(73) Assignees: Institut National de la Sante et de la Recherche Medicale, Paris (FR); Sangstat Medical Corporation, Fremont, CA (US)

( * ) Notice: Subject to any disclaimer, the term of this patent is extended or adjusted under 35 U.S.C. 154(b) by 0 days.

(21) Appl. No.: 09/958,323

(22) PCT Filed: Apr. 4, 2000

(86) PCT No.: PCT/FR00/00837

§ 371 (c)(1),
(2), (4) Date: Dec. 20, 2001

(87) PCT Pub. No.: WO00/59916

PCT Pub. Date: Oct. 12, 2000

(30) Foreign Application Priority Data

Apr. 6, 1999 (FR) .......................................... 99 04263

(51) Int. Cl.$^7$ .......................... A61K 31/66; C07F 9/32
(52) U.S. Cl. ...................................... 514/108; 558/155
(58) Field of Search ..................... 558/155; 514/108

(56) References Cited

U.S. PATENT DOCUMENTS 5,639,653 A   6/1997   Bloom et al.

FOREIGN PATENT DOCUMENTS

| WO | 95/20673 | 8/1995 |
| WO | 00/12516 | 3/2000 |
| WO | 00/12519 | 3/2000 |

OTHER PUBLICATIONS

Vlattas et al (1996): Bioorganic and Medicinal Chemistry Letters, vol. 6 (17) p 2091–2096.*
King, F.D. (1994):Med Chem: Principal & Practice, p 206–209.*
STN International, CAPLUS database, registry No. 299929–17–2.*

(List continued on next page.)

Primary Examiner—Joseph K. McKane
Assistant Examiner—Golam M. M. Shameem
(74) Attorney, Agent, or Firm—Young & Thompson

(57) ABSTRACT

The invention concerns compounds $CH_3-R_1-(CH_1)_2-R_2$ wherein: $R_1$ is selected among a tertiary alcohol; a 1,2-diol; a halohydrine; an apoxide; an alkene; an aldehyde or an α-hydroxyaldehyde; and $R_2$ is selected among a methylenediphosphonate; a difluoromethylenediphosphonate; or a monofluoromethylenediphosphoneate. The invention also concerns the uses of said compounds as selective inhibitors of Tγ9δ2 lymphocytes, and their uses, in particular for therapeutic purposes.

4 Claims, 9 Drawing Sheets

OTHER PUBLICATIONS

Chambers et al., "The Difluoromethylenephosphonate Moiety as a Phosphate Mimic: X–Ray Structure of 2–Amino–1,1–diflurorethylphosphonic Acid", Chem. Soc., Chem. Commun., 1990, pp. 1053, 1054.

Davisson et al., "Phosphorylation of Isoprenoid Alcohols", J. Org. Chem., 1986, 51, 4768–4779.

Frechet et al., Polymeric Reagents.3.Poly[vinyl(pyridinium chlorochromate)]: A New Recyclable Oxidizing Agent, J. Org. Chem, vol. 43, No. 13, 1978, pp. 2619–2620.

Gotoh et al., "Different Roles of the Diphosphonate Moieties of Allyic and Homoallylic Diphosphates in Prenyltransferase Reaction", Biochemical and Biophysical Research Communications, vol. 156, No. 1, 1988, pp. 396–402.

Morita et al., "Direct presentation of non–peptide prenyl pyrophosphate antigens to human gamma d T cells", 66th Forum in Immunology, Non–polymorphic Antigent Presentation Molecules, pp. 73–79.

Nieschalk et al., "Synthesis of Monofluoro– and Difluoromethylenephosphonate Analogues of sn–Glycerol–3–phosphate as Substrates for Glycerol–3–Phosphate Dehydrogenase and the X–Ray Structure of the Fluoromethylenephosphonate Moiety", Tetrahedron, vol. 52, No. 1, pp. 165–176, 1996.

Rubottom et al., "alpha–Hydroxy Ketones from the Oxidation of Enol Silyl Ethers with m–Chloroperbenzoic acid: 6–hydroxy–3,5,5–trimethyl–2–cyclohexen–1–one," Org. Synth. Coll. vol. 7, pp. 282–286.

Schoel et al., "Phosphate is essential for stimulation of V gamma 9 V delta 2 T lymphocytes by mycobacterial low molecular weight ligand," Eur. J. Immunol. 1994, 24:1886–1892.

Tanaka et al., "Natural and synthetic non–peptide antigens recognized by human gamma delta T cells", Nature, vol. 375, May 11, 1995, pp. 155–158.

Wucherpfennig et al., "Gamma delta T–cell receptor repertoire in acute multiple sclerosis lesions", Proc. Natl. Acad. Sci. USA vol. 89, pp. 4588–4592, May 1992 Immunology.

Yamashita et al., "Role of gamma delta T lymphocytes in the development of Behcet's disease", Clin Exp Immunol 1997:107:241–247.

Yount, "ATP Analogs".

* cited by examiner

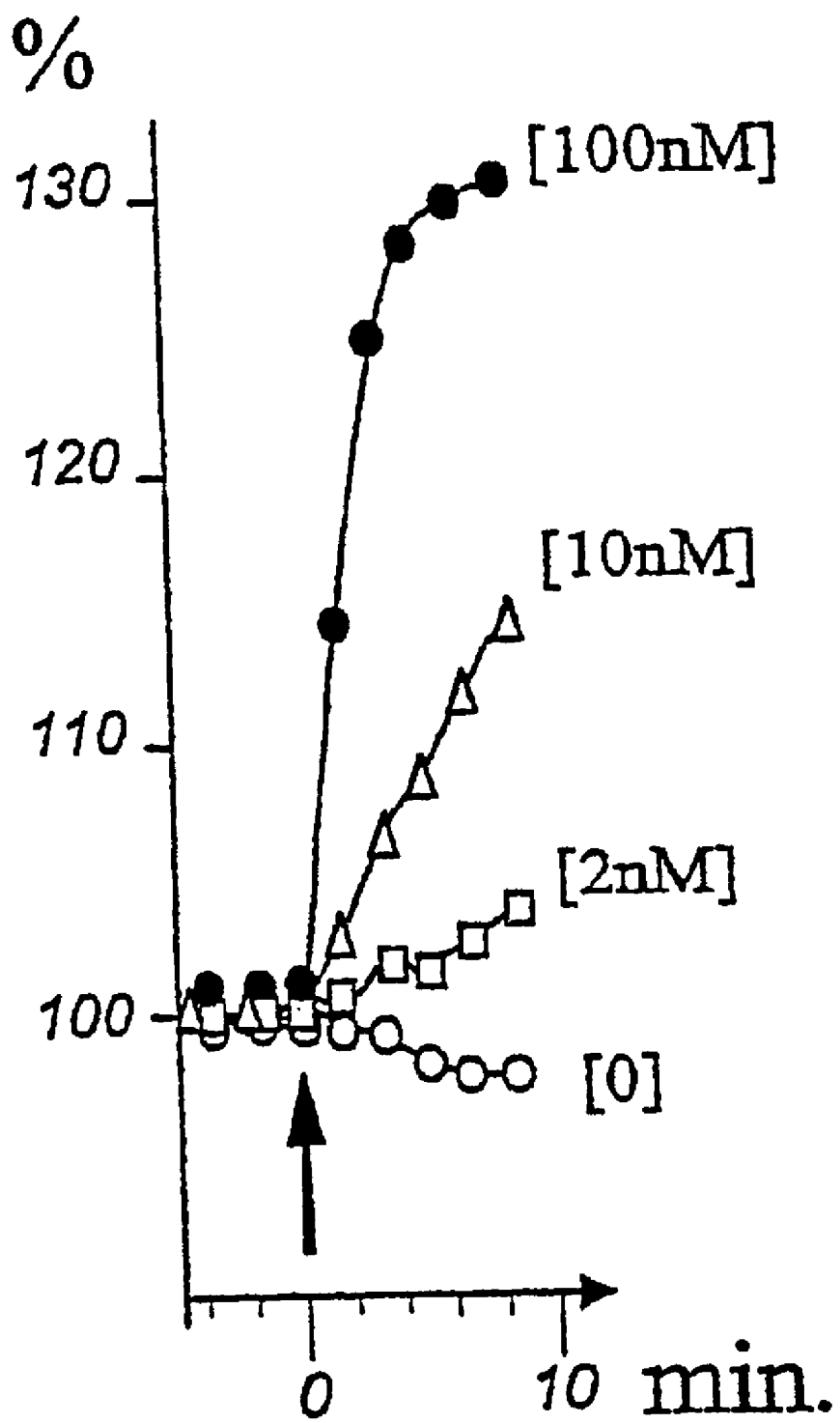

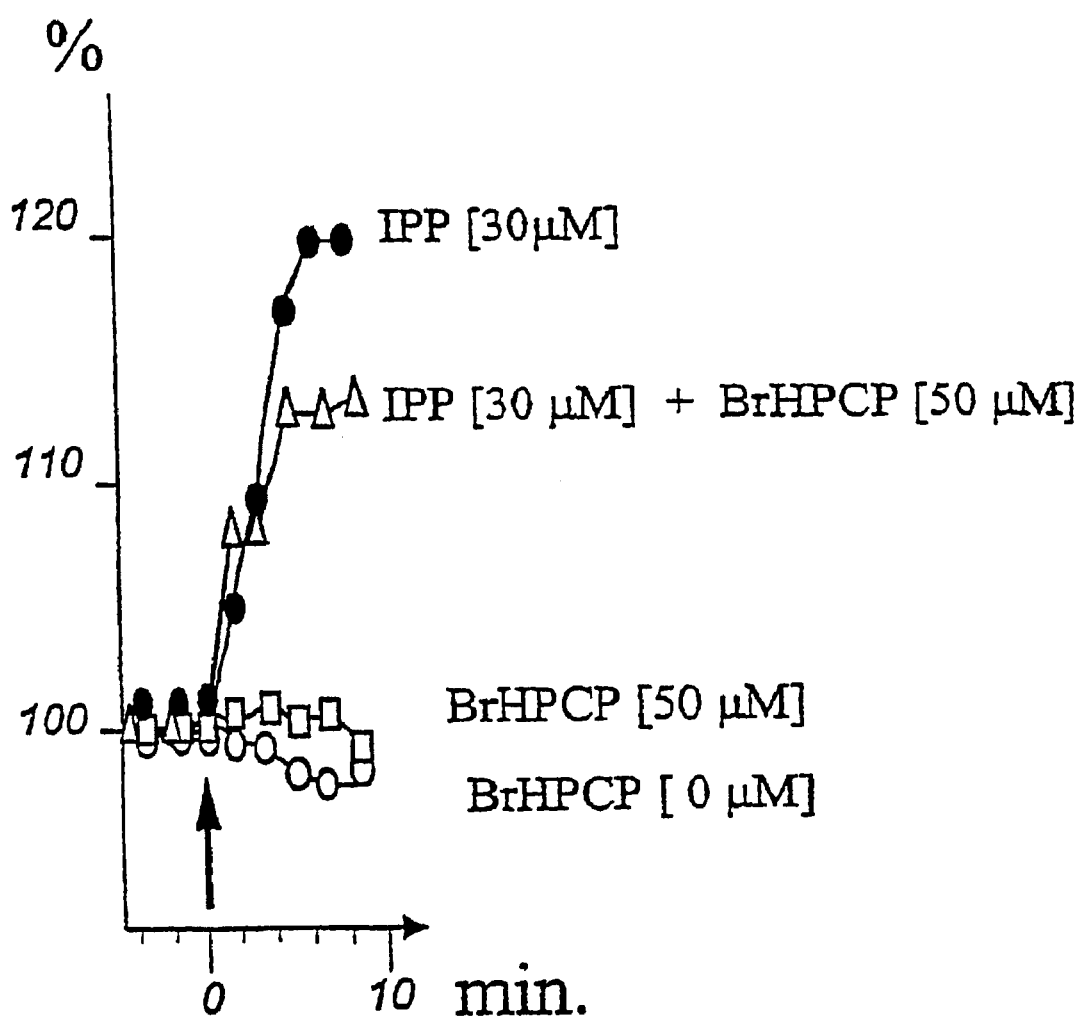

COMPOUNDS SELECTIVELY INHIBITING GAMMA 9 DELTA 2 T LYMPHOCYTES

This application is a 371 of PCT/FR00/00837 Apr. 4, 2000.

The invention relates to compounds selectively inhibiting the Tγ9δ2 lymphocytes carriers of receivers at variable regions Vγ9 and Vδ2.

The Tγδ lymphocytes of primates present in the peripheral blood (humans, monkeys) represent, in the healthy individual, conventionally 1 to 5% of the lymphocytes of the blood and play a role in the immune system. It has been shown that they recognize their antigenic ligands by direct interaction with the antigen, without presentation by molecules of CMH of a presenting cell. The Tγ9δ2 lymphocytes (sometimes also called Tγ2δ2 lymphocytes) are the Tγδ lymphocytes carrying TCR receivers at variable regions Vγ9 and Vδ2. They represent the majority of the Tγδ lymphocytes of human blood.

When they are activated, the Tγδ lymphocytes exert a strong cytotoxic activity unrestrained by CMH, particularly effective to kill various types of cells, particularly pathogenic cells. Nevertheless, the massive activation of the Tγδ lymphocytes accompanying sometimes the development of certain pathologies, can have or lead to a pathogenic character. Such is the case in particular for the auto-immune maladies such as plaque sclerosis (Wucherpfennig K. et al "γδT cell receptor repertoire in acute multiple scerosis lesion" 1992, PNAS 89, 4588) or the Behçet malady (Yamashita N. et al "Role of γδT lymphocytes in the development of Behçet disease" Clinical Experimental, Immunology, 107(2), 241–247).

Such is the case moreover for a certain number of bacterial pathologies such as brucellosis, tularemia, salmonelloses, tuberculosis, ehrlichiosis, or parasitic pathologies such as malaria (malarial attack), visceral leishmaniosis, toxoplasmosis (for example Morita C. T. et al, "Direct presentation of non peptide prenyl pyrophosphate antigens to human gamma delta T cells", 1996, Research in Immunology, Vol. 147, p 347–353).

Various antigens of Tγ9δ2 lymphocytes have been described (WO-9520673, U.S. Pat. No. 5,639,653, "Natural and synthetic non peptide antigens recognized by human γδT cells", Yoshimasa Tanaka et al, Nature, 375, 1995, pp 155–158). Nevertheless, these natural antigens are not completely identified. Moreover, it is known that the mechanism of activation of the Tγ9δ2 lymphocytes by these antigens is particular, because it does not imply any known molecule of CMH (major complex of histocompatibility). But the nature of this mechanism remains unexplained, such that the problem of adjusting inhibitors of Tγ9δ2 lymphocytes remains unsolved.

WO-95/20673 also indicates that the principals having a phosphatase enzymatic activity (phosphohydrolase phosphoric monoester and/or pyrophosphatase nucleotide and/or phosphohydrolase phosphoric diester) such as the alkaline phosphatase, are adapted to inhibit the antigenic activity of natural origin, the so-called TUBag, from a mycobacterial extract, vis-à-vis Tγ9δ2 lymphocytes. Nevertheless, this inhibition takes place by cleaving the antigens and thus does not act on the Tγ9δ2 lymphocytes themselves. Moreover, it is not specific and poses problems of uncontrollable secondary effects to the extent that the biological or physiological media themselves include numerous phosphorylated compounds and natural phosphatase enzymatic activities.

The invention thus seeks to provide compounds for selective inhibition of the Tγ9δ2 lymphocytic stimulation, which is to say specific immunosuppressive compounds for Tγ9δ2 lymphocytes.

The invention seeks more particularly to provide such compounds which will be compatible, on the one hand, with administration to a primate and, on the other hand, with considerations of profitability for industrial use (which must be produced in a simple manner, in large quantities, at an acceptable cost on an industrial scale).

Moreover, it is also desirable that the inhibition of the Tγ9δ2 lymphocytes for the treatment of an excess of activation of the Tγ9δ2 lymphocytes does not destroy definitively the immune system of the patient or of the lymphocytic biological medium. Thus, the invention also seeks to provide compounds having an inhibitory activity which will be not only selective with respect to Tγ9δ2 lymphocytes, but also reversible, such that the activity of the Tγ9δ2 lymphocytes may ultimately be restored.

The invention also seeks to provide new phosphorated compounds and their process for production.

The invention also seeks to provide applications of the compounds according to the invention for the selective and reversible inhibition of the Tγ9δ2 lymphocytes. More particularly, the invention seeks to provide applications for the compounds according to the invention for therapeutic use, of the applications of the compounds according to the invention for diagnosis, and applications of the compounds according to the invention for the experimental study of Tγ9δ2 lymphocytes, their antigens or specific immunosuppressive agents.

The invention seeks particularly to provide a treatment for pathologies implying an activation of the Tγ9δ2 lymphocytes, and particularly selected from malaria (malarial attack), visceral leishmaniosis, toxoplasmosis, brucellosis, tularemia, salmonelloses, tuberculosis, ehrlichiosis, auto-immune maladies such as sclerosis by plaques or the Behçet malady.

To do this, the invention relates to new compounds of the formula:

in which $R_1$ is selected from the following functions:

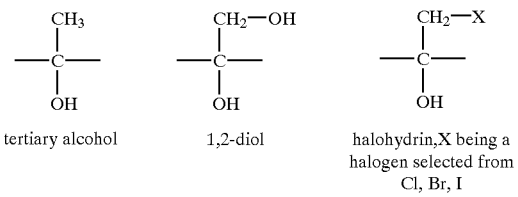

tertiary alcohol     1,2-diol     halohydrin, X being a halogen selected from Cl, Br, I

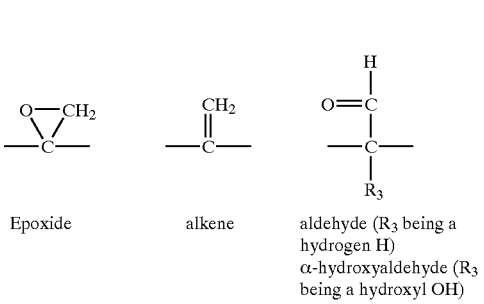

Epoxide     alkene     aldehyde ($R_3$ being a hydrogen H) α-hydroxyaldehyde ($R_3$ being a hydroxyl OH)

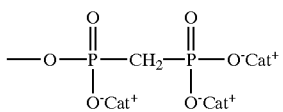

Methylenediphosphonate

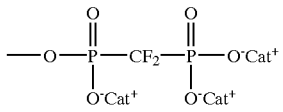

difluoromethylenediphos-Phonate

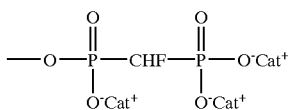

Monofluoromethylenediphosphonate and $R_2$ is selected from the following groups:
in which CAT+ represents one or more organic or mineral cations (including the proton) identical or different, in the same compound, except for 3-methyl-3-butene-1-yl-difluoromethylenediphosphonate, and 3-methyl-3-butene-1-yl-methylenediphosphonate.

The compounds according to formula (I) of the invention are the following (IUPAC nomenclature):

$R_1$: tertiary alcohol function:
   3-methyl-3-butanol-1-yl-methylenediphosphonate;
   3-methyl-3-butanol-1-yl-monofluoromethylenediphosphonate;
   3-methyl-3-butanol-1-yl-difluoromethylenediphosphonate;

$R_1$: 1,2 diol function:
   3-methyl-3,4-butanediol-1-yl-methylenediphosphonate;
   3-methyl-3,4-butanediol-1-yl-monofluoromethylenediphosphonate;
   3-methyl-3,4-butanediol-1-yl-difluoromethylenediphosphonate.

$R_1$: halohydrin function wherein X=Cl, Br, I:
   3-(chloromethyl)-3-butanol-1-yl-methylenediphosphonate;
   3-(chloromethyl)-3-butanol-1-yl-monofluoromethylenediphosphonate;
   3-(chloromethyl)-3-butanol-1-yl-difluoromethylenediphosphonate;
   3-(bromomethyl)-3-butanol-1-yl-methylenediphosphonate;
   3-(bromomethyl)-3-butanol-1-yl-monofluoromethylenediphosphonate;
   3-(bromomethyl)-3-butanol-1-yl-difluoromethylenediphosphonate;
   3-(iodomethyl)-3-butanol-1-yl-monofluoromethylenediphosphonate;
   3-(iodomethyl)-3-butanol-1-yl-methylenediphosphonate;
   3-(iodomethyl)-3-butanol-1-yl-difluoromethylenediphosphonate.

$R_1$: epoxyd function:
   3,4-epoxy-3-methyl-1-butyl-methylenediphosphonate;
   3,4-epoxy-3-methyl-1-butyl-monofluoromethylenediphosphonate;
   3,4-epoxy-3-methyl-1-butyl-difluoromethylenediphosphonate.

$R_1$: alkene function:
   3-methyl-3-butene-1-yl-methylenediphosphonate;
   3-methyl-3-butene-1-yl-monofluoromethylenediphosphonate;
   3-methyl-3-butene-1-yl-difluoromethylenediphosphonate.

$R_1$: aldehyde function ($R_3$=H):
   3-formyl-1-butyl-methylenediphosphonate;
   3-formyl-1-butyl-monofluoromethylenediphosphonate;
   3-formyl-1-butyl-difluoromethylenediphosphonate.

$R_1$: α-hydroxyaldehyde ($R_3$=OH):
   3-formyl-3-butanol-1-yl-methylenediphosphonate;
   3-formyl-3-butanol-1-yl-monofluoromethylenediphosphonate;
   3-formyl-3-butanol-1-yl-difluoromethylenediphosphonate.

The 3-methyl-3-butene-1-yl-difluoromethylenediphosphonate has been described by "phosphorylation of isoprenoid alcohols" V. Jo Davisson et al., J. Org. Chem. 1986, 51, 4775.

The invention moreover relates to compounds of formula (I) above (including 3-methyl-3-butene-1-yl-difluoromethylenediphosphonate) as to their uses as agents for the selective inhibition of Tγ9δ2 lymphocytes.

The invention relates more particularly to the compounds of formula (I) above, as to their uses as agents for the inhibition of selective phosphoantigenic activation of Tγ9δ2 lymphocytes by a phosphated antigen (phosphoantigen), such as a natural antigen (for example the Tubag disclosed by WO 95/20673), or artificial antigens such as IPP (3-methyl-3-butene-1-yl-pyrophosphate), a phosphohalohydrin compound such as BrHPP (3-(bromomethyl)-3-butanol-1-yl-diphosphate) or IHPP (3-(iodomethyl)-3-butanol-1-yl-diphosphate), or a phosphoepoxid compound such as EpoxPP (3,4 epoxy-3-methyl-1-butyl-diphosphate).

Although the real mechanism for the inhibition of Tγ9δ2 lymphocytes by the compounds of the invention is not definitely set forth, the work of the inventors permits believing that such a selective inhibition of the Tγ9δ2 lymphocytes can be obtained by compounds which satisfy the three following conditions:

1) having a molecule of topologic form corresponding to formula (I),
2) having an $R_1$ function adapted to form a covalent bond by a reaction of the nucleophile substitution or addition type, or the electrophile addition in the presence of Tγ9δ2 lymphocytes,
3) having a group structurally analogous to a pyrophosphate, but adapted to inhibit the enzymatic hydrolysis of the terminal phosphate necessary to the activation of Tγ9δ2 lymphocytes.

Such a compound can thus have the property of occupying the antigenic recognition sites of the Vγ9 Vδ2 receptors thanks to conditions 1) and 2), but preventing the transduction of the activation signal to the lymphocyte because the enzymatic hydrolysis of the terminal phosphate, which the inventors think would be necessary for this transduction, is inhibited.

The function $R_1$ is selected so as to be compatible with conditions 1) and 2) above and to permit obtaining the compound according to the invention. The $CH_3$—$R_1$—$(CH_2)_2$— group must thus be an antigenic ligand of the T Vγ9 Vδ2 receptor. It can be isopentenyl, of course, which is an antigenic ligand. The inventors have shown moreover that the other groups $CH_3$—$R_1$—$(CH_2)_2$— of the formula (I) mentioned above also permit obtaining inhibitors of the Tγ9δ2 lymphocytes.

The group $R_2$ is selected from structural analogs of pyrophosphates that are unhydrolizable or weakly hydrolizable. Such analogs of the pyrophosphates are known per se (cf. "ATP analogs" by R. G. Yount (1975) Adv. Enzymol. Vol. 43, p 1–56; "Synthesis of monofluoro- and difluoromethylenephosphonate analogues of sn-glycerol-3-phosphate as substrates for glycerol-3-phosphate dehydrogenase and the X-Ray structure of the fluoromethylenephosphonate moiety" by J. Nieschalk et al. (1996) Tetrahedon vol. 52 p165–176; "The difluoromethylenephosphate moiety as a phosphate mimic: X ray structure of 2 amino-1,1-difluoro ethylphosphonic acid" by R. D. Chambers et al. (1990) J. Chem. Soc. Chem. Commun. vol. 15, p 1053–1054).

A group $R_2$ should also be selected to be compatible with the synthesis of the compound according to the invention.

The invention also relates to uses of the compounds according to the invention as inhibitors for the Tγ9δ2 lymphocytes of primates, particularly as inhibitors of the proliferation and/or the cytotoxic activity and/or the production of mediatory substances by the Tγ9δ2 lymphocytes of the primates with TCR receptors comprising the variable regions Vγ9 and Vδ2.

The invention also relates to applications of the compounds according to the invention for the treatment of cells sensitive to Tγ9δ2 lymphocytes of primates, in a natural or artificial medium adapted to contain Tγ9δ2 lymphocytes, in which said cells can be placed into contact with these Tγ9δ2 lymphocytes, this medium being compatible with the compounds according to the invention (which is to say it is not susceptible to cause degradation at least under certain conditions of treatment).

By "cell sensitive to Tγ9δ2 lymphocytes" is meant any cell subject to the effective activity induced by Tγ9δ2 lymphocytes (cellular death, the invention permitting preventing destruction of the cells by lymphocytes); reception of salting out by the Tγ9δ2 lymphocytes (TNF-α, INF-γ . . . ); cellular proliferation induced by Tγ9δ2 lymphocytes.

The invention thus extends to a process for the selective inhibition of the Tγ9δ2 lymphocytes, particularly to a process for selective inhibition of the proliferation of Tγ9δ2 lymphocytes and/or of the cytotoxic activity of the Tγ9δ2 lymphocytes and/or the production of mediatory substances by the Tγ9δ2 lymphocytes, in which these Tγ9δ2 lymphocytes are placed in contact with at least one compound according to the invention in a medium containing Tγ9δ2 lymphocytes.

Preferably, and according to the invention, there is used at least one compound according to the invention at a concentration in the medium which gives rise to a selective inhibition of the polyclonal proliferation of the Tγ9δ2 lymphocytes. This medium can be selected from human blood, the blood of a non-human primate, extracts of human blood, and extracts of the blood of a non-human primate.

Preferably, and according to the invention, there is used a concentration greater than the IC50 concentration of the compound according to the invention, defined as that permitting reducing by 50% the intensity of the response of the Tγ9δ2 lymphocytes, according to the induced cytotoxicity test, with a standard antigenic stimulant, particularly BrHPP at 80 nM.

Said medium can be extracorporeal, said inhibition process according to the invention being then an extracorporeal treatment, which can particularly take place in the laboratory, for example by the diagnosis or the study of the Tγ9δ2 lymphocytes or of their properties. For diagnosis, the inhibition of the Tγ9δ2 lymphocytes can serve to evaluate the condition of activation of the Tγ9δ2 lymphocytes removed from a patient, according to their behavior after placing them in contact with an inhibitory quantity of a compound according to the invention.

Said medium can also be intracorporeal, the selective inhibition of the Tγ9δ2 lymphocytes being then a therapeutic or diagnostic utility.

More particularly, said medium is the peripheral blood of a primate. The invention thus includes in particular a process for the selective inhibition of Tγ9δ2 lymphocytes of the peripheral blood of a primate—particularly human—in which there is administered a quantity adapted to inhibit the Tγ9δ2 lymphocytes, of at least one compound according to the invention. There is thus administered at least one compound according to the invention by any route—notably parenteral in the peripheral blood—.

Said medium can also be a cellular site to be treated, and there is administered at least one compound according to the invention directly in contact with the cellular site to be treated (topical administration).

Thus, the invention includes applications of the compounds according to the invention therapeutically for the curative or preventive treatment of pathologies involving an activation of the Tγ9δ2 lymphocytes of primates in a medium that can contain Tγ9δ2 lymphocytes.

The invention thus also relates to the compounds of the formula (I) for their use as active therapeutic substances in primates. The invention also relates to the use of the compounds according to formula (I), for their use in a therapeutic composition adapted to be administered to a primate for the preventive or curative treatment of a pathology involving the activation of Tγ9δ2 lymphocytes.

The invention relates in particular to therapeutic uses of the compounds according to the invention for the treatment of pathologies of primates belonging to the group formed by parasitoses selected from malaria (paludism), visceral leishmaniosis and toxoplasmosis; auto-immune maladies—particularly plaque scleroses and the Behçet malady—involving an activation of the Tγ9δ2 lymphocytes; bacterial pathologies selected from brucellosis, tularemia, salmonelloses, tuberculosis, and ehrlichiosis. According to the invention, there is administered a therapeutic composition adapted to release, in the peripheral blood and/or at a cellular site to be treated, a quantity of at least one compound according to the invention adapted to inhibit the Tγ9δ2 lymphocytes.

Thus, it has been shown generally in the prior art mentioned above, that a composition having the property of inhibiting Tγ9δ2 lymphocytes can be preferably used for the treatment of these pathologies.

Conventionally, in all the texts, the terms "therapy" or "therapeutic" include not only the curative treatments or care, but also the preventive treatments (prophylaxis) such as vaccination. Thus, by permitting selective inhibition of the Tγ9δ2 lymphocytes, the invention permits immunostimulation treatments that can preferably also serve as prophylaxis by preventing the development of Tγ9δ2 lymphocytes, as well as curing by inhibiting Tγ9δ2 lymphocytes.

The invention thus also relates to a therapeutic or diagnostic composition comprising at least one compound according to the invention. More particularly, the invention relates to a therapeutic compound comprising a quantity suitable to be administered to a primate—particularly in contact with the peripheral blood or by topical route—of at least one compound according to the invention—particularly for the preventive or curative treatment of the above-mentioned pathologies. A composition according to the invention can be an immunostimulatory composition, or a vaccine, the compounds according to the invention being antigens selectively inhibiting the Tγ9δ2 lymphocytes.

A therapeutic composition according to the invention can be prepared in galenic form adapted to be administered by any route, particularly by the parenteral route directly into the peripheral blood of the primate, with at least one compound according to the invention in a quantity adapted to inhibit the Tγ9δ2 lymphocytes and one or several suitable excipients. Given the active concentration of the compounds according to the invention (of the order of 10 to 1000 $\mu$M), such an administration is to be envisaged without the risk of toxicity.

A therapeutic composition according to the invention can also be prepared in a suitable galenic form for its topical administration, directly in contact with the Tγ9δ2 lymphocytes.

The galenic form of a therapeutic composition according to the invention is prepared according to the selected route of administration, by conventional techniques for galenic formulation. The quantity and the concentration of the compound or compounds according to the invention, and the posology, are determined by reference to the known chemotherapeutic treatments of the maladies to be treated, given the bioactivity of the compounds according to the invention relative to the Tγ9δ2 lymphocytes, of the individual to be treated, and of the malady in question, and of the different biological effects.

Preferably, and according to the invention, there is administered the compound according to the invention in a quantity adapted to create in the peripheral blood of the patient a concentration greater than the IC50 concentration of the compound according to the invention as defined above.

Preferably, and according to the invention, for a bioactive compound at a concentration comprised between 1 $\mu$M and 1000 $\mu$M, there is administered by any route a quantity of a compound or compounds according to the invention comprised between 0.1 mg and 1 g—particularly between 1 mg and 100 mg—per kilogram of weight of the patient.

Moreover, it has been shown in vitro that the compounds according to the invention have no general toxicity. Moreover, it is known that the biochemical category of molecules to which the compounds according to the invention belong (phosphoesters) constitute a family of compounds compatible with analogous and physiological biological media. The compounds according to the invention have thus no other toxic effects than those induced by their bioactivity on the Tγ9δ2 lymphocytes.

Moreover, the compounds according to the invention have a sufficiently low molecular weight (particularly below 500) to be compatible with their elimination by renal or urinary route.

An example of formulation of an injectable therapeutic composition according to the invention for a primate of 1 kg is the following:

5 mg of sodium salt of 3,4-epoxy-3-methyl-1-butyl-methylenediphosphonate (Epox-PCP) diluted in 5 ml of sterile Ringer-Lactate buffer.

There is thus administered over 4 days: 1 dose per day of 5 mg for 1 kg of animal, corresponding to a concentration in the circulating blood of 50 mg/l, which can be greater than the IC50 concentration of 15 $\mu$M for Epox-PCP (a concentration of 50 mg/l corresponding to about 160 $\mu$M).

It is to be noted that most of the excipients or other conventional acceptable pharmaceutical additives used, are chemically compatible with the compounds according to the invention.

A therapeutic composition according to the invention can also preferably comprise one or several other active principles, particularly to provide a synergetic effect. In particular, a compound according to the invention can serve as a vaccine adjuvant. The vaccine therapeutic composition according to the invention is thus comprised by a known vaccine composition to which is added a quantity of compound according to the invention adapted to inhibit the Tγ9δ2 lymphocytes which will not be able to exert their direct effective activity (for example cytotoxic), nor regulatory of the Th-1 type (for example salting out interferon and tumoral necrosis factor (TNF or "tumor necrosis factor")), and thereby promoting the lymphocyte B responses (for example production of antibodies).

The invention also extends to the use of at least one compound according to the invention for the production of a therapeutic composition according to the invention. More particularly, the invention bears on the use of at least one compound according to the invention for the production of a therapeutic composition adapted for the preventive or curative treatment of a pathology involving an activation of the Tγ9δ2 lymphocytes of primates—particularly a pathology selected from the group mentioned above—. In this instance, the invention also extends to the use of at least one compound according to the invention for the production of a therapeutic composition adapted to be administered—particularly in contact with the peripheral blood or by topical route—to a primate—notably human—for the preventive or curative treatment of a pathology as mentioned above.

The invention also relates to a process for the production of a composition—particularly a therapeutic composition—according to the invention, having the property of selectively inhibiting Tγ9δ2 lymphocytes, in which there is used at least one compound according to the invention. The invention also relates to a process for the production of a therapeutic composition adapted for the preventive or curative treatment of a pathology as mentioned above, in which there is used at least one compound according to the invention. The invention bears in particular on a process for production of a therapeutic composition adapted to be administered—particularly in contact with the peripheral blood or by topical route, to a primate for the preventive or curative treatment of a pathology such as mentioned above, in which there is used at least one compound according to the invention.

The compounds according to the invention can be prepared according to the reactions given hereafter, according to the different R1 and R2g groups.

In the reaction diagrams, PCP identifies the methylenediphosphonate group, PCHFP identifies the monofluoromethylenediphosphonate group, and PCF$_2$P identifies the difluoromethylenediphosphonate group.

Reaction I

For R$_1$: tertiary alcohol function, alkene, epoxyd, and R$_2$: PCP, PCHFP, PCF$_2$P:

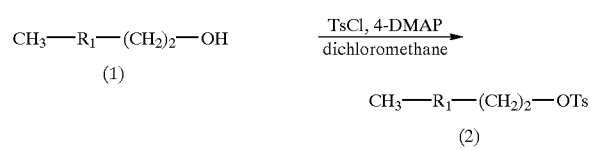

-continued

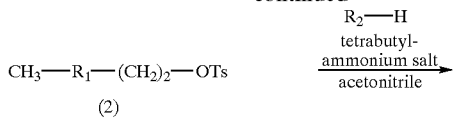
(2)

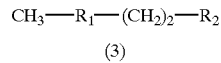
(3)

in which Ts is tosyl, TsCl is tosyl chloride, 4-DMAP is 4-dimethylaminopyridine.

The tetrabutylammonium salts of the reagent $R_2$—H, used in a quantity at least equal to 2 molar equivalents, are, according to the group $R_2$ of the compound to be prepared:

- for PCP: the tris(tetra-n-butylammonium) hydrogeno-methylene-diphosphonate prepared from methylene disphosphonic acid,
- for $PCF_2P$: the tris(tetra-n-butylammonium) hydrogeno-difluoromethylene-diphosphonate prepared from tetrakis(trimethylsilyl)-difluoromethylenedisphosphonate according to the procedure described by V. Jo DAVISSON et al. J. Org. Chem, 51, p 4768–4779, (1986),
- for PCHFP: the tris(tetra-n-butylammonium) hydrogeno-monofluoromethylenediphosphonate prepared from tetrakis(trimethylsilyl)-monofluoromethylenediphosphonate according to the procedure described by J. NIESCHALK et al. (1996) Tetrahedron vol. 52 p165–176 and adapted according to V. Jo DAVISSON et al. J. Org. Chem., 51, p 4768–4779, (1986).

The alcohols (1) are commercially available products except the alcohol corresponding to the R1 epoxyd function which can be obtained easily (G. M. RUBOTTOM et al., Org. Synth. Coll. Vol 7, p 282 (1990), Wiley) by epoxydation of the alkene function as follows:

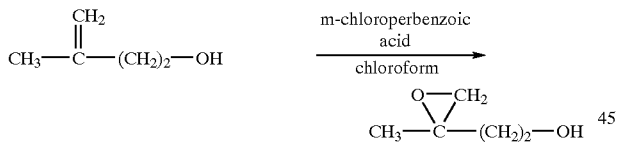

(1) wherein $R_1$: alkene function (1) wherein $R_1$: epoxyd function

Formula II

For $R_1$: Halohydrine function (X=Cl, Br, I), and $R_2$: PCP, PCHFP, $PCF_2P$:

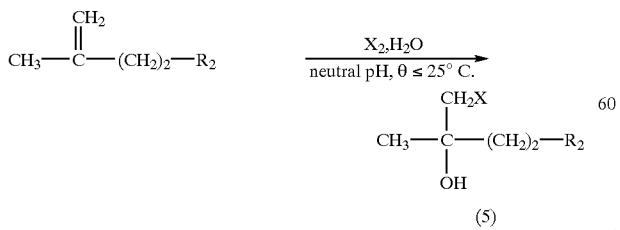

(3) wherein $R_1$: alkene function

Reaction III

Variant for $R_1$: epoxyd function, and $R_2$: PCP, PCHFP, $PCF_2P$:

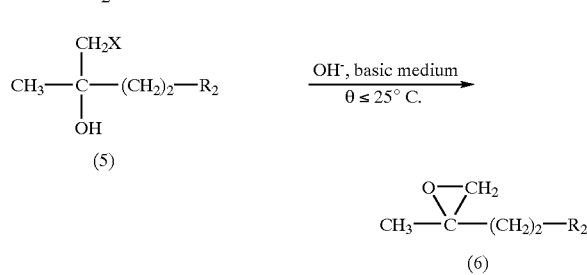

Reaction IV

For $R_1$: 1,2-diol function, and $R_2$: PCP, PCHFP, $PCF_2P$:

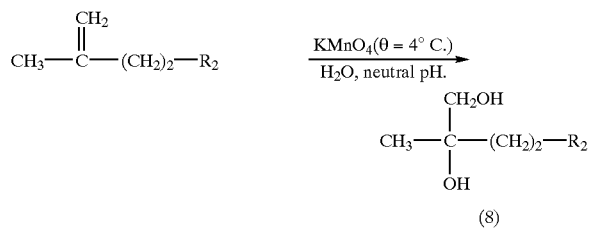

(3) wherein $R_1$: alkene function in which $KMnO_4$ is potassium permanganate (in a quantity less than or equal to 1 molar equivalent)

Reaction V

For $R_1$: aldehyde function, and $R_2$: PCP, PCHFP, $PCF_2P$:

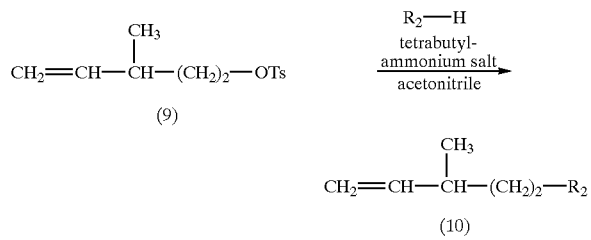

in which $R_2$—H is used in a quantity at least equal to 2 molar equivalents.

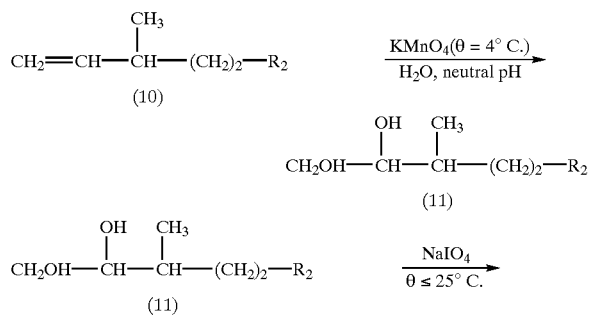

-continued

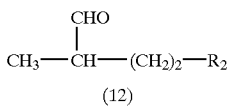

(12)

The compound (9) can be easily obtained in the form of an alcohol by the Grignard reaction between an alkenyl organomagnesium and formaldehyde or ethylene oxide, for example starting from 1-chloro-2-methyl-3-butene.

Reaction VI

For $R_1$: α-hydroxyaldehyde function, and $R_2$: PCP, PCHFP, PCF$_2$P:

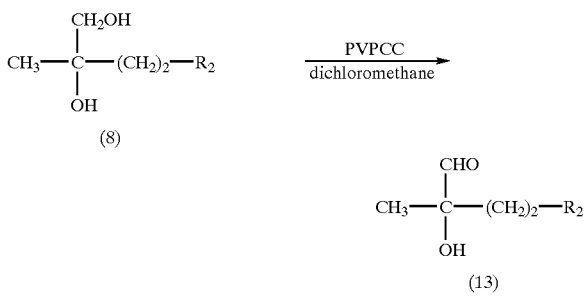

in which PVPCC is Poly[vinyl(pyridinium chlorochromate)], as indicated by FRECHET J. M., WARNOCK J., and FARRALL J., J Org. Chem, vol 43, No. 13, p2618–21 (1978).

Other characteristics, objects, and advantages of the invention will become apparent from a reading of the examples which follow, given by way of non-limiting example, and the accompanying drawings, in which:

FIGS. 10a, 10b and 10c show the results obtained in Example 14.

EXAMPLE 1

Production of 3-Methyl-3-butene-1-yl-methylenediphosphonate (IPCP)

Preparation of 3-Methyl-3-butene-1-yl-tosylate

Figure 1:
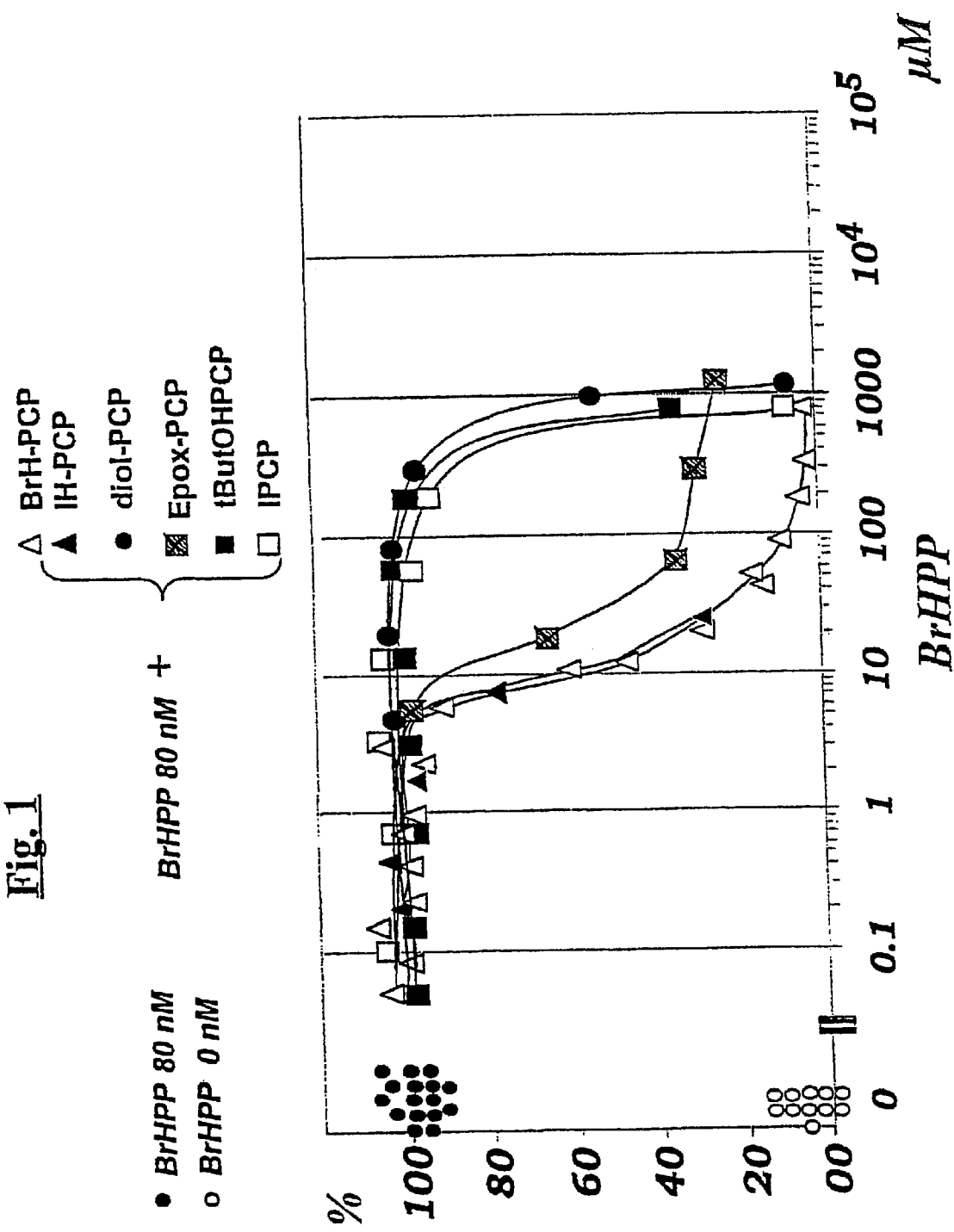
FIGS. 1 to 6 are graphs representing the results obtained in Example 10.

Into a glass reactor provided for manipulation under an inert atmosphere and carefully dried, are introduced with magnetic agitation (2.32 mmoles–442mg) of tosyl chloride and (2.55 mmoles–312 mg) of 4-(N,N-dimethylamino) pyridine in 5 ml of anhydrous dichloromethane. To this mixture is added slowly with the help of a syringe and with means of a septum (2.32 mmoles–200 mg) of isopentenol in solution in about 1 ml of dichloromethane. The reaction is followed by chromatography on thin layer silica (silica gel 60 F-254—eluant: pentane/ethyl acetate 85/15 v/v—Rf(R-Ots)=0.4 and Rf(TsCl)=0.5). After about 3 hours of agitation under a nitrogen atmosphere, the reaction mixture is diluted in a large volume of hexane (about 100 ml) which gives rise to the immediate formation of a white precipitate. The mixture is then filtered and the filtrate concentrated by evacuation under reduced pressure. The solution is diluted with a little diethyl ether and again filtered. After evaporation of the solvent, there is obtained a yellowish oil. The product is purified by chromatography on a preparative silica column (silica gel 60—eluant: pentane/ethyl acetate 85/15). (1.98 mmoles–475 mg) of 3-methyl-3-butene-1-yl-tosylate (85% of yield as isolated product) are thus obtained. The compound (colorless oil) is stored at +4° C. in an anhydrous medium.

Preparation of tris(tetra-n-Butylammonium) Hydrogeno-methylenediphosphonate

There is prepared a solution containing (5.68 mmoles–1 g) of methylenediphosphonic acid in about 20 ml of deionized water. To this acid solution (pH 1.0), there is added dropwise an aqueous solution of tetra-n-butylammonium hydroxide (Bu$_4$NOH) at 40% by weight until there is obtained a pH value equal to 10.0. After lyophilization of the titrated solution, there is obtained about 5 g of the salt of tetra-n-butylammonium (hygroscopic salt with an oily appearance) which is dissolved in 10 ml of anhydrous acetonitrile. The saline solution is then filtered and dried by successive evaporations of the solvent under reduced pressure. There is thus obtained a solution of tris(tetra-n-butylammonium) hydrogen-methylenediphosphonate with a purity equal to 97% (result deduced by analysis by ion chromatography—HPAEC). The volume is adjusted with the anhydrous acetonitrile so as to obtain a concentration of salt comprised between 0.5 and 1 M. The solution is stored at −20° C. in anhydrous medium.

Preparation of 3-Methyl-3-butene-1-yl-methylenediphosphonate (Isopentenyl Methylenediphosphonate)

In a carefully dried glass reactor, there is introduced under a nitrogen atmosphere, 2.5 ml of a solution of tris(tetra-n-butylammonium) hydrogen-methylenediphosphonate of 0.7 M (1.75 mmoles) in anhydrous acetonitrile. The reactor is cooled by an ice bath and then there is added with magnetic agitation and with the help of a syringe (0.70 mmoles–168 mg) of 3-methyl-3-butene-1-yl-tosylate in solution in a minimum quantity of acetonitrile (0.5–1M). After introduction of the tosylate, the ice bath is withdrawn and then the reaction is continued with agitation at ambient temperature. The progress of the reaction is then followed by ionic chromatography (HPAEC) on an IonPac® AS11 column. After about 3 hours, the solvent is evaporated under reduced pressure and the reaction medium redissolved in 3 ml of a mixture of water/2-propanol 98/2 (v/v). The solution is passed through a column containing (19 mequiv–4 g) of cationic resin DOWEX® 50-WX8-200 (NH$_4^+$ form) then eluted with 10 ml of the mixture of water (pH 9)/2-propanol 98/2 (v/v). After lyophilization, there is recovered a white solid containing the raw product.

Purification

Excess ammonium diphosphonate and a small proportion of inorganic salts are separated from the reaction medium by co-precipitation in the presence of ammonium hydrogencarbonate. The raw product obtained in the preceding step is dissolved in 4 ml of ammonium hydrogencarbonate 0.1 M which is transferred into a centrifugation tube of 25 ml. The solution is then treated with 10 ml of a mixture of acetonitrile/2-propanol 1/1 (v/v) by agitating the mixture vigorously (vortex) for several minutes until the formation of a precipitate. The tube is then centrifuged at 2000 rpm at 10° C. for 5 minutes. The supernatant, in which are extracted the inorganic salts, is reserved at +4° C. The procedure is repeated by redissolving the precipitate in 3 ml of ammonium hydrogencarbonate 0.1 M to which are added 7 ml of the acetonitrile/2-propanol mixture. After elimination of the solvent from the combined supernatants in a rotative evaporator, there is obtained an oily liquid which is reserved at +4° C.

The ammonium tosylate is for the most part separated from the reaction mixture by extraction with the chloroform/methanol solvent 1/1 (v/v). The oily liquid from the preceding step is dissolved in 4 ml of deionized water at pH 9 and treated with 1 ml of this solvent by a conventional extraction procedure repeated 3 times. Then there are eliminated from the aqueous phase the traces of solvent by evaporation under reduced pressure at 30° C. The solution is stored at −20° C.

The product is ultimately purified as needed by ion exchange chromatography on cartridges of Sep-Pak Accell Plus QMA (Waters®) in an amount of 360 mg with 10 grams eluted successively with aqueous solutions of ammonium hydrogencarbonate respectively of 20 mM, 40 mM, 100 mM, then 200 mM followed b chromatography (HPAEC) of the eluted fractions. The fractions corresponding to the purified product are combined and then lyophilized. For carrying out biological tests, the aqueous solutions of the product are sterilized by filtration on a 0.2 μm filter and stored at −20° C. In the case of tests carried out in vivo, the solutions are first passed over a cationic resin column DOWEX® 50-WX8-200 ($Na^+$ form) eluted with two volumes of the column of deionized water.

Analysis of the ammonium salt by mass spectrometry with so-called "electrospray" (negative mode) ionization:

ESI-MS: m/z=243 $[M-H]^-$ pseudomolecular species; ESI-MS/MS of the $[M-H]^-$ ion: m/z=225 (loss of $H_2O$); m/z=157 (pyrophosphonate).

EXAMPLE 2

Production of 3-(Bromomethyl)-3-butanol-1-yl-methylenediphosphonate (BrHPCP)

0.34 mmoles (100 mg) of 3-methyl-3-butene-1-yl-methylenediphosphonate (ammonium salt) in solution in 2 ml of deionized water of neutral pH are treated under a suction hood with 1.9 ml of a saturated aqueous solution (0.18 M) of bromene water (1 equivalent–0.34 mmoles of bromene). The bromene water is added progressively and preferably to a cold solution of ammonium salt by acting by periodically agitating until the bromene water is decolorized. In the case in which the bromene is added in slight excess (persistent yellow coloration), the solution is transferred into a glass flask and then placed for several minutes under reduced pressure (rotating evaporator) at a temperature of 30° C. until the color disappears. The product, 3-(bromomethyl)-3-butanol-1-yl-methylenediphosphonate is generated quantitatively (0.33 mmoles–130 mg)—which result is deduced from analysis by ionic chromatography—HPAEC. The solution is then treated as in Example 1 for carrying out biological tests and stored at −20° C.

Analysis of the almonium salt by mass spectrometry with ionization, so-called "electrospray" (negative mode):

ESI-MS: m/z=339, 341 natural isotopes of bromene present in the pseudomolecular species $(M-H)^-$ ESI-MS/MS of the $[M-H]^-$ ion: m/z=259 (intramolecular rearrangement)

EXAMPLE 3

Production of 3-(Iodomethyl)-3-butanol-1-yl-methylenediphosphonate (IHPCP)

Preparation of Iodized Water:

A solution of iodized water of the order of 0.5 to 1 mM is prepared by prolonged sonication (about 15 minutes) of several iodine crystals in a solution of deionized water, with filtration. For tests bearing on the largest quantities, more concentrated iodine solutions can be obtained by adding a small proportion of alcohol to the initial aqueous solution. The iodized water is then titrated with sodium thiosulfate with the use of starch as a color indicator.

Preparation of 3-(iodomethyl)-3-butanol-1-yl-methylenediphosphonate:

5 μmoles (1 ml of a 5 mM solution) of 3-methyl-3-butene-1-yl-methylenediphosphonate prepared according to Example 1 in the form of the ammonium salt in aqueous or hydroalcoholic medium of neutral pH, are treated at ambient temperature by the addition of 1 equivalent of iodine in aqueous solution (5 ml iodized water at 1 mM). The solution is held for 30 minutes at ambient temperature, then 30 minutes at +4° C. carrying out vigorous periodical agitation. After decoloration of the iodized water, the product 3-(iodomethyl)-3-butanol-1-yl-methylenediphosphonate is generated quantitatively. For carrying out biological tests, the solution is first concentrated by lyophilization and treated as in Example 1.

EXAMPLE 4

Production of 3,4-Epoxy-3-methyl-1-butyl-methylenediphosphonate (Epox PCP)

There is treated at ambient temperature, 1 ml of an aqueous solution containing (2 mg–5.1 μmoles) of 3-bromomethyl)-3-butanol-1-yl-methylenediphosphonate (ammonium salt) prepared according to Example 2, with 0.5 ml of an ammoniac molar solution. The solution is maintained under agitation for several minutes and then lyophilized to eliminate the ammonia. The dry residue obtained after lyophilization is redissolved in 1 ml of deionized water and purified by ion exchange chromatography on cartridges of Sep-Pak Accell Plus QMA (Waters®) of 360 mg as described in Example 1.

Analysis of the ammonium salt by mass spectrometry with so-called "electrospray" (negative mode) ionization:

ESI-MS: m/z=259 $[M-H]^-$ pseudomolecular species; ESI-MS/MS of the $[M-H]^-$ ion: m/z=241 (loss of $H_2O$); m/z=157 (pyrophosphonate)

EXAMPLE 5

Production of 3-Methyl-3-butanol-1-yl-methylenediphosphonate (tButOHPCP)

According to a procedure analogous to that described in Example 1, there is prepared in a first step 3-methyl-3-butanol-1-yl-tosylate from 3-methyl-1,3-butanediol. The 3-methyl-3-butanol-1-yl-methylenediphosphonate is obtained by reacting 0.5 mmole of tosylate and 1 mmole of tris(tetra-n-butylammonium) hydrogen-methylenediphosphonate at ambient temperature for 24 hours. The purification procedure is identical to that described in Example 1.

Analysis of the ammonium salt by mass spectrometry with so-called "electrospray" (negative mode) ionization:

ESI-MS: m/z=261 $[M-H]^-$ pseudomolecular species; ESI-MS/MS of the $[M-H]^-$ ion: m/z=243 (loss of $H_2O$); m/z=157 (pyrophosphonate)

EXAMPLE 6

Production of 3-Methyl-3,4-butanediol-1-yl-methylenediphosphonate (Diol PCP):

In glass flask, there is introduced 1 ml of an aqueous solution of neutral pH of the ammonium salt of 3-methyl-3-butene-1-yl-methylenediphosphonate (3.4 μmoles–1 mg)—prepared according to Example 1—to this solution are added several fractions, 680 μl of a cold solution of potassium permanganate of 5 mM (1 equivalent–3.4 μmoles) while agitating periodically the solution in a cold hcamber (+4° C.). After about 40 minutes of reaction during which a brown precipitate of manganese dioxide forms, there are added several microliters of a saturated aqueous solution of isopantenol. The manganese dioxide is separated from the reaction mixture by centrifugation and then filtration. The filtrate is purified by ion exchange chromatography on cartridges of Sep-Pak Accell Plus QMA (Waters®) of 360 mg as described in Example 1.

EXAMPLE 7

Production of 3-Methyl-3-butene-1-yl-difluoromethylenediphosphonate (IPCF$_2$P)

This product is prepared as described in Example 1, by reacting in anhydrous acetonitrile, 0.5 mmole of 3-methyl-3-butene-1-yl-tosylate with (3 equivalents–1.5 mmoles) of the salt of tris(tetra-n-butylammonium) prepared according to the protocol described by V. Jo Davisson et al. J. Org. Chem., 1986, 51 p 4768–4779.

Analysis of the ammonium salt by mass spectrometry with so-called "electrospray" (negative mode) ionization:

ESI-MS: m/z=279 [M-H]$^-$ pseudomolecular species; ESI-MS/MS of the [M-H]$^-$ ion: m/z=261 (loss of H$_2$O); m/z=193 (pyrophosphonate)

EXAMPLE 8

Production of 3-(Bromomethyl)-3-butanol-1-yl-difluoromethylenediphosphonate (BrHPCF$_2$P)

This product is obtained by a reaction of 3-methyl-3-butene-1-yl-difluoromethylenediphosphonate (prepared according to Example 7) with bromanated water by following the process described in Example 2.

Analysis of the ammonium salt by mass spectrometry with so-called "electrospray" (negative mode) ionization:

ESI-MS: m/z=375,377 natural isotopes of bromene present in the pseudomolecular species [M-H]$^-$; ESI-MS/MS of the [M-H]$^-$ ion: m/z=295 (intramolecular rearrangement)

EXAMPLE 9

Production of 3,4-Epoxy-3-methyl-1-butyl-difluoromethylenediphosphonate (Epox PCF$_2$P)

This product is obtained by treatment in basic medium of 3-(bromomethyl)-3-butanol-1-yl-difluoromethylenediphosphonate (prepared according to Example 8) by following the procedure described in Example 4.

Analysis of the ammonium salt by mass spectrometry with so-called "electrospray" (negative mode) ionization:

ESI-MS: m/z=295 [M-H]$^-$ pseudomolecular species; ESI-MS/MS of the [M-H]$^-$ ion: m/z=277 (loss of water); m/z=193 (difluoromethylenediphosphonate)

EXAMPLE 10

Measurement of the Cytotoxic Activity of a Tγ9δ2 Clone Activated by 80 nM of BrHPP, or Unactivated The specific cytotoxic activity of a clone of Tγ9δ2 lymphocytes, measured according to the induced cytotoxicity test, is compared, this activity being stimulated with 80 nM of the antigen 3-(bromomethyl)-3-butanol-1-yl-diphosphate (BrHPP) (small black dots in the upper left of FIG. 1), and considered as the reference response (100%), relative to that of a culture of clones that are not stimulated (0%) (small white dots FIG. 1).

The curves of FIG. 1 show the percentage of residual response (induced cytotoxicity test) obtained in cultures stimulated by 80 nM of BrHPP in the presence of different concentrations (on the abscissa) of the compounds according to the invention, namely BrHPCHFP (white triangles), IHPCP (black triangles), PCP Diol (black circles), PCP Epox (crossed gray squares), tButOHPCP (black squares), and IPCP (white squares), as obtained in the preceding examples.

It will be noted that the addition of increasing concentrations of these compounds inhibits up to 100% the reference response.

The tests carried out as indicated above on different compounds according to the invention permit defining their IC50 concentrations, expressed in micromoles in the following table, leading to the inhibition of 50% of the reference response of the lymphocytes stimulated by 80 nM of the compound BrHPP according to the induced cytotoxicity test.

| Compound | μM |
|---|---|
| I PCP | 700 |
| tButOH PCP | 1000 |
| Epox PCP | 30 |
| BrH PCP | 15 |
| IH PCP | 15 |
| I PCF$_2$P | 1000 |
| Epox PCF$_2$P | 300 |
| BrH PCF$_2$P | 150 |

Other similar tests have also been carried out with monofluorinated analogous compounds (in which the group R$_2$ is monofluoromethylenediphosphonate) BrHPCHFP and Epox PCHFP. These compounds are bioactive (which is to say selectively inhibit the Tγ9δ2 lymphocytes), with a bioactivity of 30 μM for BrHPCHFP and of 50 μM for Epox PCHFP, for a concentration of BrHPP equal to 150 μM.

Figure 2:
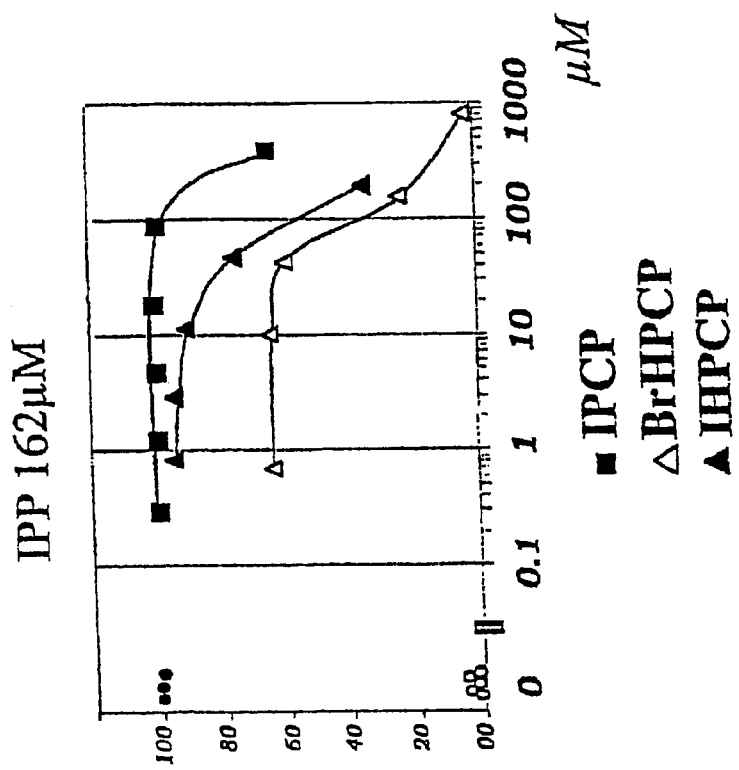
Figure 3:
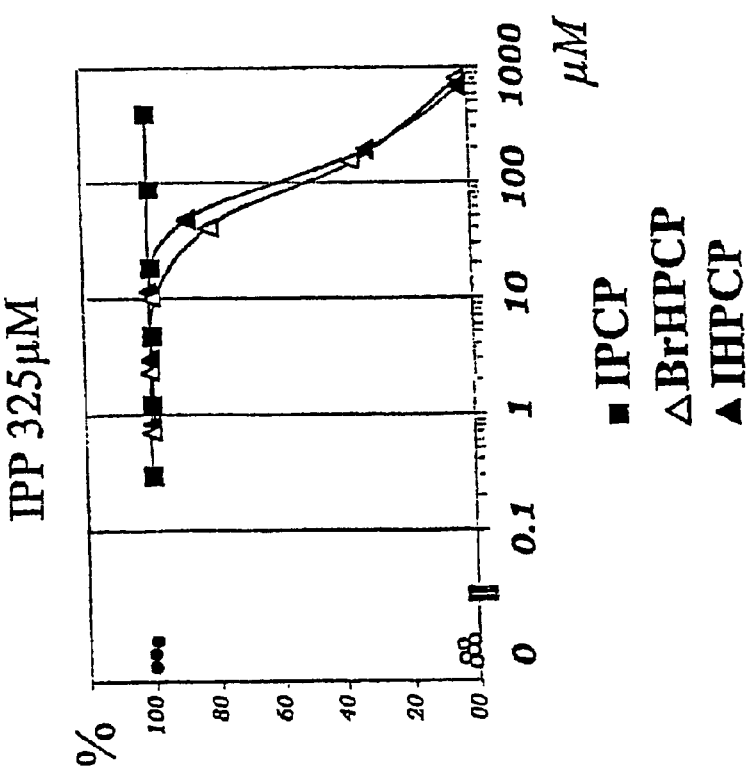

FIGS. 2 and 3 are graphs similar to FIG. 1 obtained by replacing the BrHPP antigen with the IPP antigen (isopentenylpyrophosphate) at 325 μM or, respectively, at 162 μM. The compounds according to the invention used were in these examples IPCP (black squares), BrHPCP (white triangles) and IHPCP (black triangles). As will be seen, the inhibition by the compounds according to the invention does not depend on the antigen used to stimulate the Tγ9δ2 lymphocytes.

Figure 4:
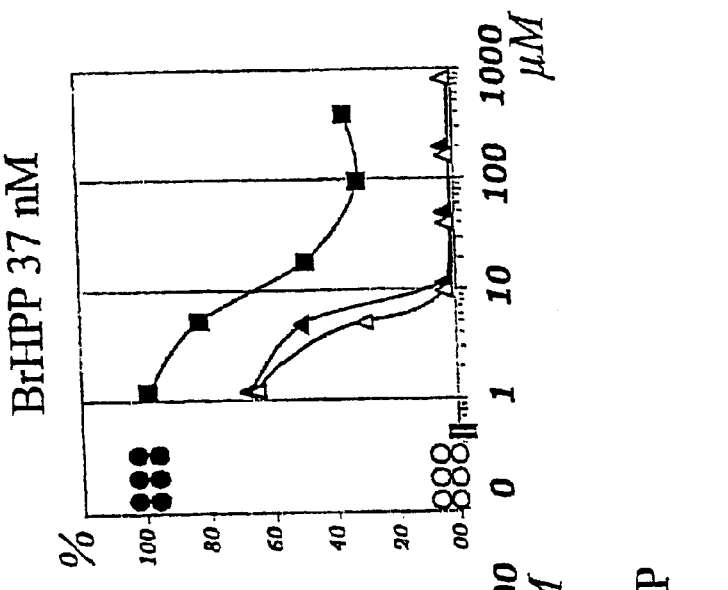
Figure 5:
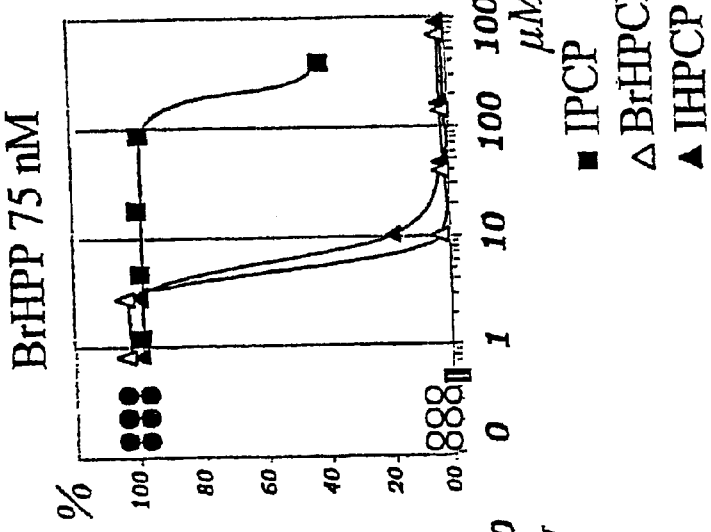
Figure 6:
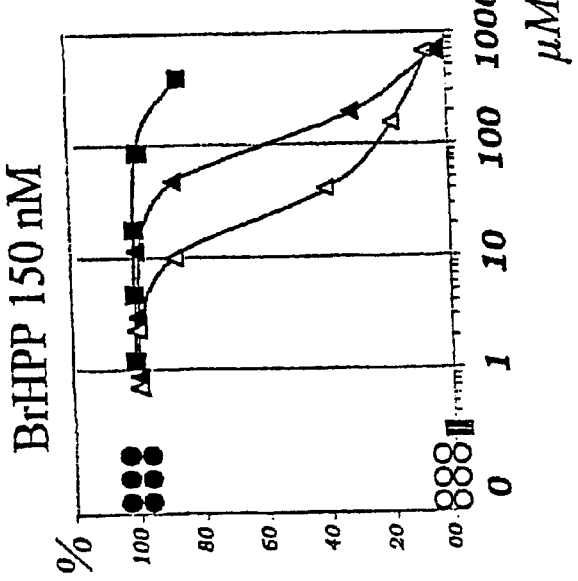

FIGS. 4 to 6 show the results obtained with these same three compounds according to the invention but when using as the antigen stimulating the Tγ9δ2 lymphocytes, the compound BrHPP at a varying concentration, respectively, of 150 μM, 75 μM and 37 μM. As will be seen, the compounds according to the invention produce the inhibition of lymphocytes in all cases, but at concentrations which vary in the same sense as the concentrations of stimulation antigen used. Stated otherwise, the greater the concentration of stimulating antigen, the greater must be the concentration of the compound according to the invention necessary to inhibit the lymphocytes.

EXAMPLE 11

Figure 7:
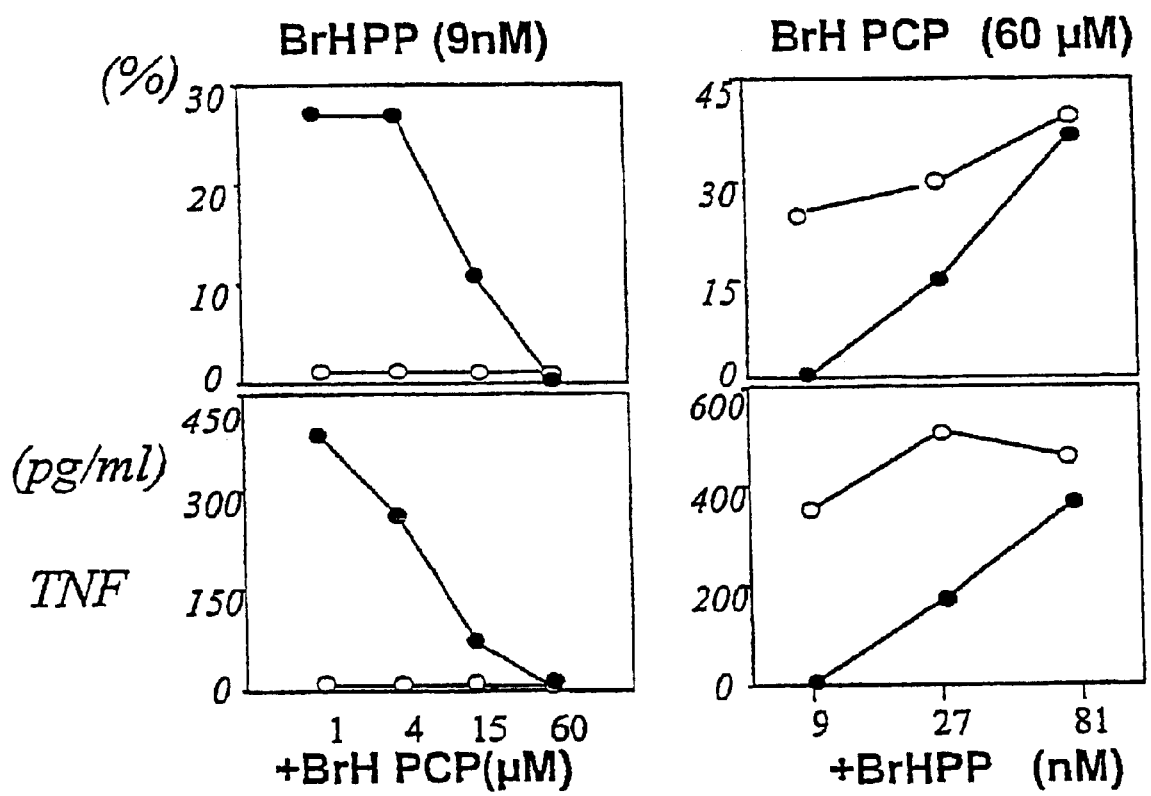
FIG. 7 shows four graphs showing the results obtained in Example 11.

Measurement of the Inhibitory Activity and its Reversible Character, by the Test of Induced Cytotoxicity and the Test of TNF Salting Out FIG. 7 shows four graphs showing the inhibition by the compound according to the invention BrHPCP and the restoration of the stimulating antigen activity of BrHPP.

The two left graphs are obtained by stimulating the Tγ9δ2 lymphocytes as in Example 12, by adding first 9 nM of BrHPP antigen into the culture medium, then by adding increasing concentrations (on the abscissa) of the compound according to the invention, BrHPCP. The two right hand graphs are obtained by incorporating first of all 60 μM of the compound according to the invention, BrHPCP, into the culture medium in contact with the Tγ9δ2 lymphocytes, then by adding increasing concentrations (on the abscissa) of the antigen compound stimulating BrHPP. The values obtained are represented by black circles. The black circles give the values obtained in the absence of the initial compound (BrHPP on the left graphs, BrHPCP on the right graphs). The upper graphs give the percentage of residual response in the cultures (induced cytotoxicity test). The lower graphs give the concentration of TNF salted out in pg/ml.

As will be seen, the compound according to the invention BrHPCP inhibits the stimulation by BrHPP, but this inhibition is reversible to the extent to which, after inhibition by the compound according to the invention BrHPCP, the stimulation is restored by adding BrHPP.

This reversible character of the inhibition of the Tγ9δ2 lymphocytes by the compounds according to the invention is important from the therapeutic point of view. Thus, following a treatment of massive activation of pathogenic character of the Tγ9δ2 lymphocytes, thanks to a compound according to the invention (for example during a malaria attack or on a tumor), the immune system of the patient is not necessarily definitively degraded and afterward can be rapidly restored.

EXAMPLE 12

BrHPCP is not an Inhibitor of Tγ8δ3 Lymphocytes

Figure 8:
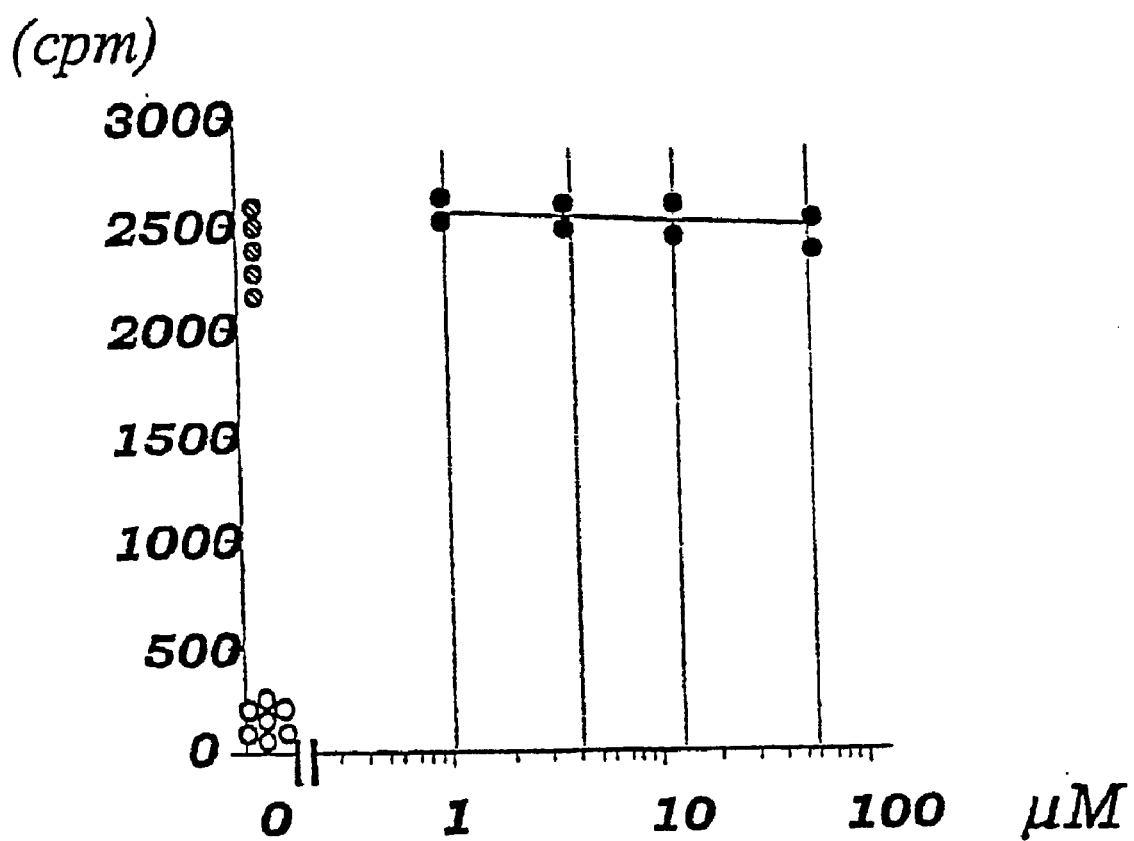
FIG. 8 shows a graph showing the results obtained in Example 12.

A test of induced cytotoxicity is carried out as in Example 12, but with a clone of Tγ8δ3 lymphocyte stimulated by a conventional antigen of these lymphocytes (black circles), and in the presence of the compound according to the invention BrHPCP in increasing concentrations in the culture medium (black squares in FIG. 8). As is seen in FIG. 8, the compound according to the invention does not inhibit the Tγ8δ3 lymphocytes. It is thus a specific inhibitor for Tγ9δ2 lymphocytes.

EXAMPLE 13

Figure 9:
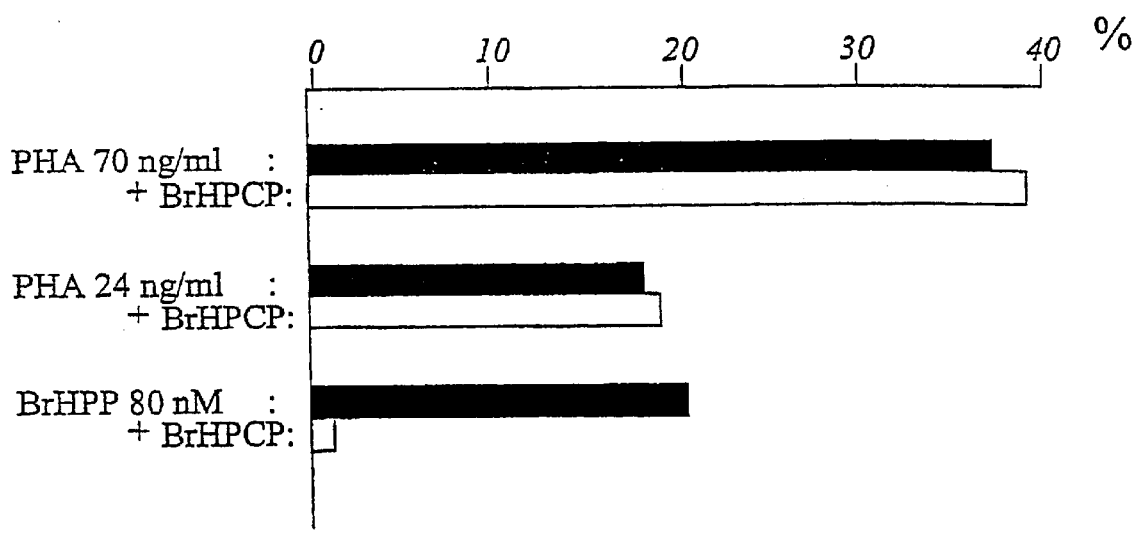
FIG. 9 shows a graph showing the results obtained in Example 13.

In this example, there is carried out a test of induced cytotoxicity on target cells P815 by a clone of Tγ9δ2 lymphocytes stimulated either by phytohemaglutinin A (PHA), which is a non-specific stimulant and is non-phosphated, for the Tγ9δ2 lymphocytes, at 70 ng/ml and at 24 ng/ml, or by the antigen BrHPP at 80 nM. The stimulant is used alone (white bars in FIG. 9) or in the presence of the inhibitor compound according to the invention, BrHPCP, at 70 μM (black bars in FIG. 9).

As will be seen, the compound according to the invention does not inhibit the lymphocytes activated by the non-specific stimulant PHA. It thus inhibits the Tγ9δ2 lymphocytes only if they have first been stimulated in a specific manner by a phosphated antigen (phosphoantigen) such as BrHPP.

EXAMPLE 14

A million Tγ9δ2 lymphocytes are deposited in a well of 10 μl of a microphysiometer (CYTOSENSOR ® apparatus sold by MOLECULAR DEVICES, USA). Their speed of metabolism given by the apparatus is measured each 30 seconds. There is added In the wells a composition comprising either the antigen BrHPP at 0, 2, 10 and 100 μM (FIG. 10a), or BrHPCP—at 2, 10, 100 μM (white circles, squares and triangles in FIG. 10b), or the antigen IHPP (3-(iodomethyl)-3-butanol-1-yl-diphosphate) at 10 nM (black circles in FIG. 10b), as a reference, or a controlled inactive composition (white circles in FIG. 10c), or BrHPCP at 50 μM alone (white circles in FIG. 10c), or IPP (isopentenylpyrophosphate) alone at 30 μM (black circles in FIG. 10c), or IPP at 30 μM and BrHPCP at 50 μM (white triangles in FIG. 10c).

Figure 10B:
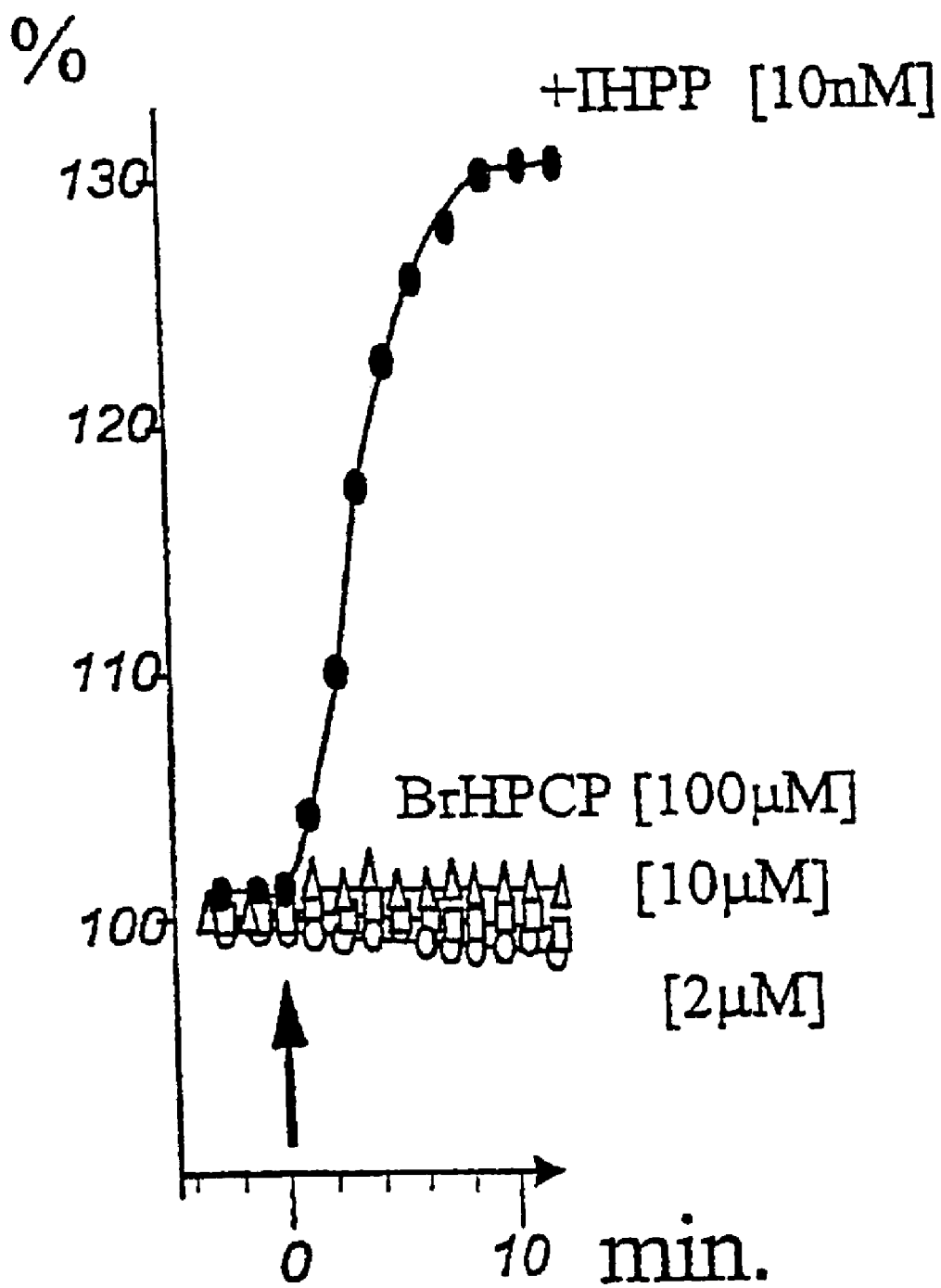

The time of addition of the compositions is represented by the arrow in FIGS. 10a, 10b, 10c.

As will be seen, compared to the response detected upon addition of the antigens, the compounds according to the invention do not induce a response (FIG. 10b) and decrease the response to phosphoantigens (FIG. 10c) of the Tγ9δ2 lymphocytes.

Continuing the experiment of FIG. 10c over a long period of time also shows that the time during which the Tγ9δ2 lymphocytes are activated is also decreased in the presence of compounds according to the invention.

What is claimed is:

1. New compounds of the formula:

in which $R_1$ is selected from the following functions:

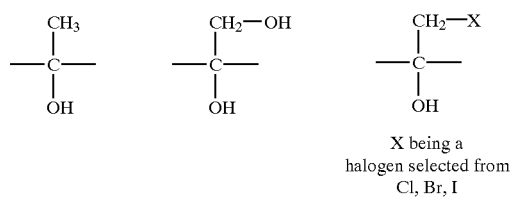

X being a halogen selected from Cl, Br, I and $R_2$ is selected from one of the following groups:

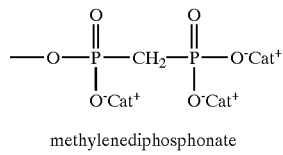

methylenediphosphonate

-continued

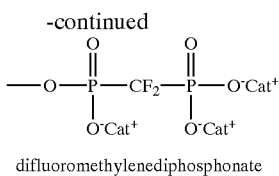

difluoromethylenediphosphonate

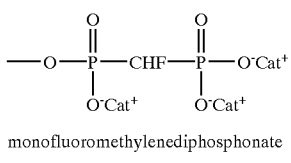

monofluoromethylenediphosphonate in which Cat+ represents one or more organic or mineral cations, comprising the proton, identical or different, in the same compound, excepting 3-methyl-3-butene-1-yl-difluoromethylenediphosphonate, and 3-methyl-3-butene-1-yl-methylenediphosphonate.

2. Compounds of the formula:

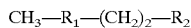

in which $R_1$ is selected from the following functions:

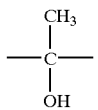 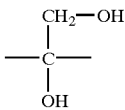 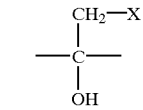

X being a halogen selected from Cl, Br, I and $R_2$ is selected from one of the following groups:

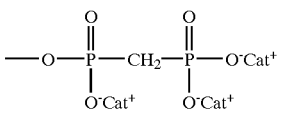

methylenediphosphonate

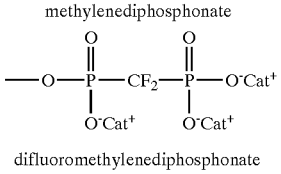

difluoromethylenediphosphonate

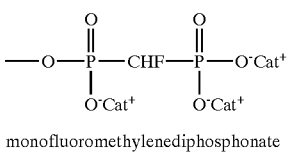

monofluoromethylenediphosphonate in which Cat+ represents one or more organic or mineral ions including the proton, identical or different, in the same compound, for their use as selective inhibitory agents for Tγ9δ2 lymphocytes.

3. Compounds according to claim 1 for their use as active therapeutic substances.

4. Compounds according to claim 1, for their use in a therapeutic composition adapted to be administered to a primate for the treatment of a pathology implying the activation of Tγ9δ2 lymphocytes.

* * * * *